(12) United States Patent
Rasimas et al.

(10) Patent No.: US 6,369,894 B1
(45) Date of Patent: Apr. 9, 2002

(54) MODULAR FLUOROMETER

(75) Inventors: Jeffrey P. Rasimas, Naperville; Michael J. Fehr, Geneva; John E. Hoots, St. Charles, all of IL (US)

(73) Assignee: NALCO Chemical Company, Naperville, IL (US)

( * ) Notice: Subject to any disclaimer, the term of this patent is extended or adjusted under 35 U.S.C. 154(b) by 0 days.

(21) Appl. No.: 09/563,086

(22) Filed: May 1, 2000

(51) Int. Cl.[7] .............................................. G01N 21/25
(52) U.S. Cl. ...................... 356/417; 356/418; 356/73; 356/318; 250/458.1; 436/174
(58) Field of Search ................................ 356/417, 317, 356/318, 73; 250/458.1, 459.1, 461.1; 436/174, 43, 164, 807

(56) References Cited

U.S. PATENT DOCUMENTS

| | | | | |
|---|---|---|---|---|
| 4,861,163 A | * | 8/1989 | Bach | 356/417 |
| 5,436,718 A | * | 7/1995 | Fernandes et al. | 356/73 |
| 5,756,292 A | * | 5/1998 | Royer et al. | 435/6 |
| 6,071,748 A | * | 6/2000 | Modlin et al. | 436/174 |

FOREIGN PATENT DOCUMENTS

DE (11)248 879 A1 8/1987

OTHER PUBLICATIONS

"Improved Multilaser/Multiparameter Flow Cytometer for Analysis & Sorting of Cells & Particles", John Steinkamp, et al., Rev. Sci. Instrum., 62(11), Nov. 1991, pp. 2751–2764.

\* cited by examiner

*Primary Examiner*—Frank G. Font
*Assistant Examiner*—Layla Lauchman
(74) *Attorney, Agent, or Firm*—Margaret M. Brumm; Thomas M. Breininger (57) ABSTRACT

Described and claimed is a modular fluorometer and a method of using same to control an industrial water system, wherein said modular fluorometer comprises:

one or more units with each unit comprising:

a channel comprising an optically appropriate cell through which a water sample flows;

a light source positioned outside said optically appropriate cell;

an optional excitation filter positioned between the light source and the optically appropriate cell;

a reference detector positioned outside the optically appropriate cell;

an emission detector positioned outside the optically appropriate cell;

an optional emission filter positioned between said emission detector and said optically appropriate cell;

wherein if more than one unit is present in said modular fluorometer, said optically appropriate cells through which said water sample flows are aligned such that only one channel through which a water sample flows exists in said fluorometer.

14 Claims, 4 Drawing Sheets

MODULAR FLUOROMETER

FIELD OF THE INVENTION

The present invention relates generally to devices and methods for monitoring the presence or concentrations of additives to natural or industrial water systems. More specifically, the present invention relates to a modular fluorometer, which can be used to detect one or more fluorophores in water from a natural or an industrial water system.

BACKGROUND OF THE INVENTION

The use of fluorophores in industrial water systems or in hydrology in general is known. The use of inert fluorescent tracers for determining the hydraulic losses in an industrial water system is known. Furthermore, using fluorescent tracers for controlling additive or product dosage to a recirculating or once-through cooling water system is also known (see U.S. Pat. No. 4,783,314). In this method, a fluorescent tracer is combined with one or more additives in a known proportion of tracer to additive(s) and then the mixture is added to the water of a cooling system. A fluorometer is then used to detect the presence and concentration of the fluorescent tracer in the cooling water and therefore the presence and concentration of the amount of additive.

A fluorometer is an analytical device that essentially comprises a light source, a means of selecting the desired excitation wavelength range, a sample cell, a means of selecting the desired emission wavelength range, and a detector. A spectrofluorometer is a specific type of fluorometer where the means for selecting the excitation and/or emission wavelength range is performed by a grating. A grating acts to disperse a continuum of light into its components. Spectrofluorometers may be further subdivided into scanning spectrofluorometers, those that use a mechanical means to scan the wavelength spectrum based on the position of the grating relative to the excitation source and/or emission (this describes a standard laboratory model fluorometer), or fixed spectrofluorometers where the grating is fixed with respect the emission. The emission (fluorescence) is then directed to an array of detectors. The array of detectors could be charge coupled devices, usually abbreviated "CCD" or the array of detectors could be photodiodes. The detectors are then calibrated in the appropriate wavelength units. A commercial device such as this is available from Ocean Optics (available from Drysdale and Associates, Inc., P.O. Box 44055, Cincinnati, Ohio 45244 (513) 831-9625). This type of fixed spectrofluorometer still requires the appropriate excitation wavelength selection device, which could be a scanning grating or filter.

The fluorometers that are most suitable for use under field conditions are not grating spectrofluorometers, rather, they are filter-based fluorometers. A filter-based fluorometer uses a filter to exclude all but the selected wavelength range. Most currently available filter-based fluorometers have one channel with this channel containing an optically appropriate cell.

A light source and an optional excitation filter, are positioned on one side of the optically appropriate cell and an emission detector, and an emission filter are positioned on the opposite side of the optically appropriate cell. A reference detector may optionally be present. Because fluorescence is isotropic, most fluorometers detect any fluorescent light emitted from the fluorophore at a 90° angle from the light source in order to minimize collection of any spurious excitation light.

The excitation filter permits light of the chosen excitation wavelength range to pass through the filter and into the cell. When conducting off-line batch testing, a sample of water, from a natural or an industrial water system, is placed and held in the optically appropriate cell. When conducting on-line testing the sample of water flows through the optically appropriate cell. The light is absorbed by the fluorophore present in the water sample, which, in turn, emits a fluorescent light (hereinafter known as a fluorescent signal) having the same or a longer wavelength than the excitation light. The emission filter, which is positioned between the emission detector and the optically appropriate cell, is chosen so as to permit only the light emitted by the fluorophore (the fluorescent signal of the fluorophore) to pass through the filter to the emission detector.

A limitation of currently available filter-based fluorometers is that most of them are capable of detecting only a single fluorophore species. This is because the use of a photodiode requires the use of an emission filter specifically designed to permit the passage of the fluorescent signal emitted by a single fluorophore.

The detection of a plurality of fluorophore species can be important because it is often desirable to add a plurality of additives or chemicals or inert fluorescent tracers to an industrial water system.

Another reason for needing a fluorometer capable of measuring more than one fluorescent signal is that certain fluorescent signals emitted by certain non-inert fluorophores are designed to change in response to interactions with other components of an industrial water system. Therefore, an analysis of the different fluorescent signals emitted by a single fluorophore would require the use of a plurality of currently known fluorometers.

Using a plurality of currently known fluorometers is expensive and very often not a practical, field-acceptable solution to this problem. Several other practical solutions to this problem are described in the following text.

There are known fluorometers that are "multisignal-detector-one-channel" fluorometers. These fluorometers have one channel with more than one set of light source/filter/detectors and thus are capable of measuring more than one fluorescent signal in a water sample. One such type of "multisignal-detector-one-channel" fluorometer includes a photodiode array as opposed to an individual photodiode. The problem is that photodiode arrays are expensive and fragile when used in an industrial environment such as a cooling tower or boiler water system. Accordingly, many operators of industrial water systems are reluctant to employ such an expensive and fragile piece of equipment in a hostile environment. As a result, operators, in certain circumstances, have been forced to employ a number of different fluorometers for a single industrial water system. This method is disadvantageous due to the size, cost and bulk of the required fluorometers.

A specific type of multisignal-detector-one-channel" fluorometer is described in "Improved Multilaser/Multiparameter Flow Cytometer for Analysis and Sorting of Cells and Particles, by Steinkamp et al., *Rev. Sci. Instrum.* (1991), 62(11), 2751–64. The fluorometer described therein requires expensive and fragile components. Therefore, this fluorometer is not practical or suitable for field work.

The practical difficulty in using these available filter-based fluorometers is that they can only measure what they have been set up to measure and once the light source, detector and filters have been set up it takes time and effort to change any of these elements to make the fluorometer capable of measuring fluorescent signals at other wavelengths of light.

As a result of the perceived deficiencies in existing fluorometers, there exists a need for an improved fluorometer which is capable of detecting one or more fluorophores using a single apparatus, with the capability of rapidly changing the operating setup of the fluorometer so that the desired fluorescent signals can be detected. Still further, there is a need for a method for detecting one or more fluorophores in a system utilizing such a single fluorometer.

SUMMARY OF THE INVENTION

The first aspect of the instant claimed invention is a modular fluorometer comprising:
   one or more units with each unit comprising:
   a channel comprising an optically appropriate cell through which a water sample flows;
   a light source positioned outside said optically appropriate cell;
   an optional excitation filter positioned between the light source and the optically appropriate cell;
   a reference detector positioned outside the optically appropriate cell;
   an emission detector positioned outside the optically appropriate cell;
   an optional emission filter positioned between said emission detector and said optically appropriate cell;
   wherein if more than one unit is present in said modular fluorometer, said optically appropriate cells through which said water sample flows are aligned such that only one channel through which a water sample flows exists in said fluorometer.

The second aspect of the instant claimed invention is a method of detecting the presence of one or more fluorophore species in a water sample wherein each of said fluorophore species emit light of different emission spectra after being illuminated with light defined by different excitation spectra, the method comprising the steps of:
   a) providing the modular fluorometer of the first aspect of the instant claimed invention, wherein said modular fluorometer has sufficient units to detect the presence of each fluorophore species in said water sample;
   b) moving a water sample comprising the fluorophores through each respective optically appropriate cell;
   c) illuminating said water sample with the respective light source in each unit;
   d) detecting each fluorophore species by detecting the emission spectra with the respective emission detectors in each unit.

The third aspect of the instant claimed invention is a method of controlling an industrial water system comprising using the modular fluorometer of the first aspect of the instant claimed invention, wherein said modular fluorometer further comprises a controller with said controller comprising isolated analog inputs such that the controller is capable of using the measured fluorescent signals provided by the modular fluorometer and input from other analytical devices to control an industrial water system.

DETAILED DESCRIPTION OF THE PRESENTLY PREFERRED EMBODIMENTS

Throughout this patent application the following words have the indicated meanings:

A "fluorophore" is: a molecule that, upon absorption of a photon of energy (hv) that results in an electron being promoted from the molecular electronic ground state ($S_0$) to an electronic excited state ($S_1$ or $S_2$ or $S_3$) and subsequently relaxing to the lowest vibronic state of excited state $S_1$, emits a photon of energy "E" (hv) that is lower in energy (though longer in wavelength) than was absorbed. Note that this relationship can be illustrated with the equation: $E_{(absorption)} > E_{(fluorescence)}$. This emission of energy results in the molecular electronic state being returned to the ground state ($S_0$). The overall process results in emission of fluorescent photons in an isotropic distribution. The fluorophores capable of being detected by the instant claimed fluorometer must be capable of absorbing excitation light in the wavelengths of from about 200 nm to about 1200 nm and emitting it at a longer wavelength than the excitation light.

"Inert" refers to the fact that an inert fluorophore is not appreciably or significantly affected by any other chemistry in the cooling water system, or by the other system parameters such as metallurgical composition, microbiological activity, biocide concentration, heat changes or overall heat content. To quantify what is meant by "not appreciably or significantly affected", this statement means that an inert fluorophore has no more than a 10% change in its fluorescent signal, under conditions normally encountered in cooling water systems. Conditions normally encountered in cooling water systems are known to people of ordinary skill in the art of cooling water systems.

"Isotropic" refers to the fact that if a moiety is considered a point source, and excitation light is directed at the moiety, fluorescent light is emitted equally over 360 degrees, creating, in effect, a sphere in 3 dimensions. Because of the isotropic distribution of fluorescent light, in practice, collection of the fluorescent light signal usually occurs at 90° relative to the excitation (photon) source to minimize the photons (light) collected that are attributed to the excitation (photon) source. This also helps to minimize light scattering.

"nm" means nanometers; which are $10^{-9}$ meters.

The present invention provides an improvement to the prior art in that it provides rugged, inexpensive to manufacture and compact modular fluorometers that are capable of detecting from one to sixteen separate fluorophores from the same water sample. These modular fluorometers comprise one or more units with each unit comprising:
   a channel comprising an optically appropriate cell through which a water sample flows;
   a light source positioned outside said optically appropriate cell;
   an optional excitation filter positioned between the light source and the optically appropriate cell;

a reference detector positioned outside the optically appropriate cell;

an emission detector positioned outside the optically appropriate cell;

an optional emission filter positioned between said emission detector and said optically appropriate cell;

wherein if more than one unit is present in said modular fluorometer, said optically appropriate cells through which said water sample flows are aligned such that only one channel through which a water sample flows exists in said fluorometer.

Figure 1:
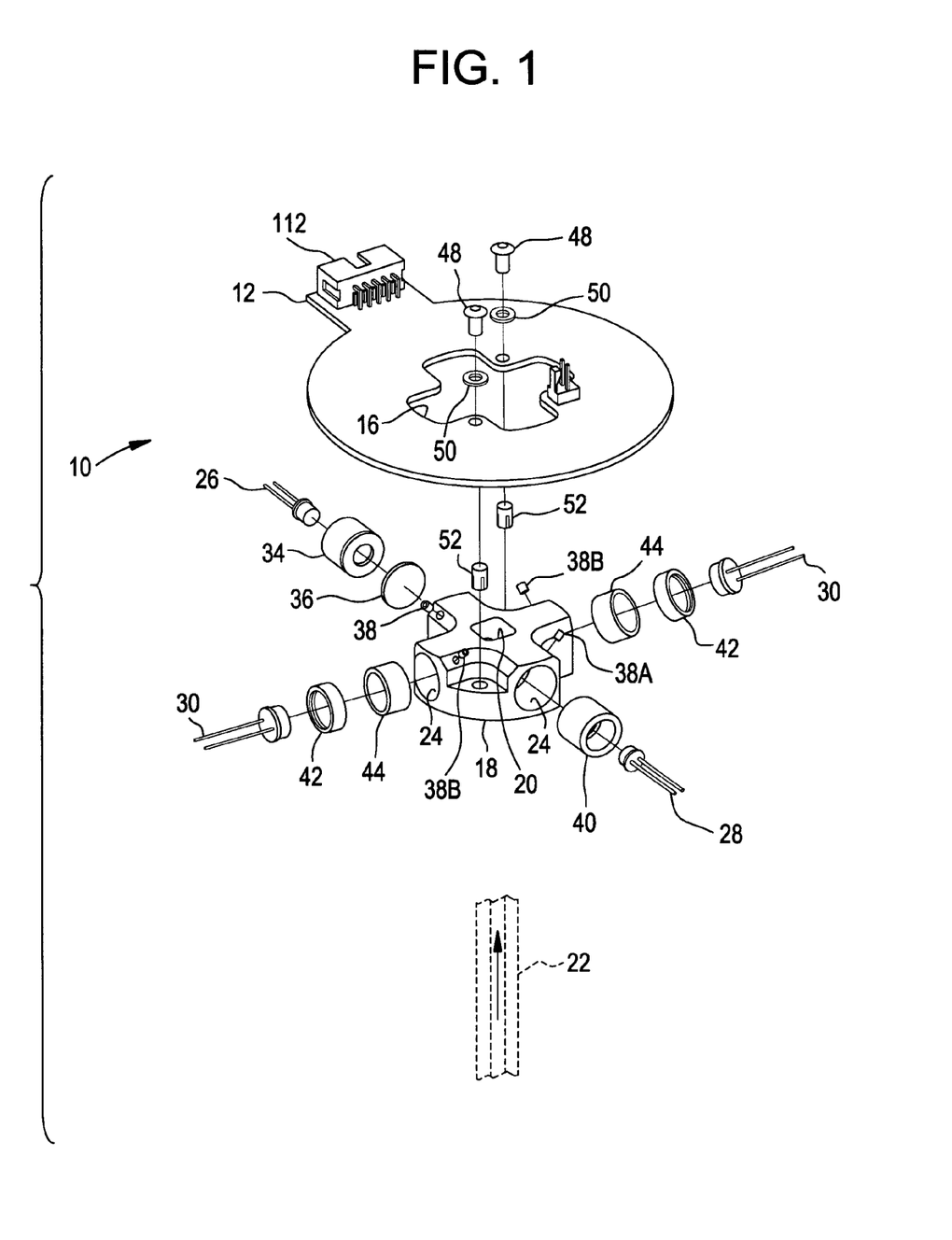
FIG. 1 is an exploded view of one unit of a modular fluorometer made in accordance with the present invention.
Figure 2:
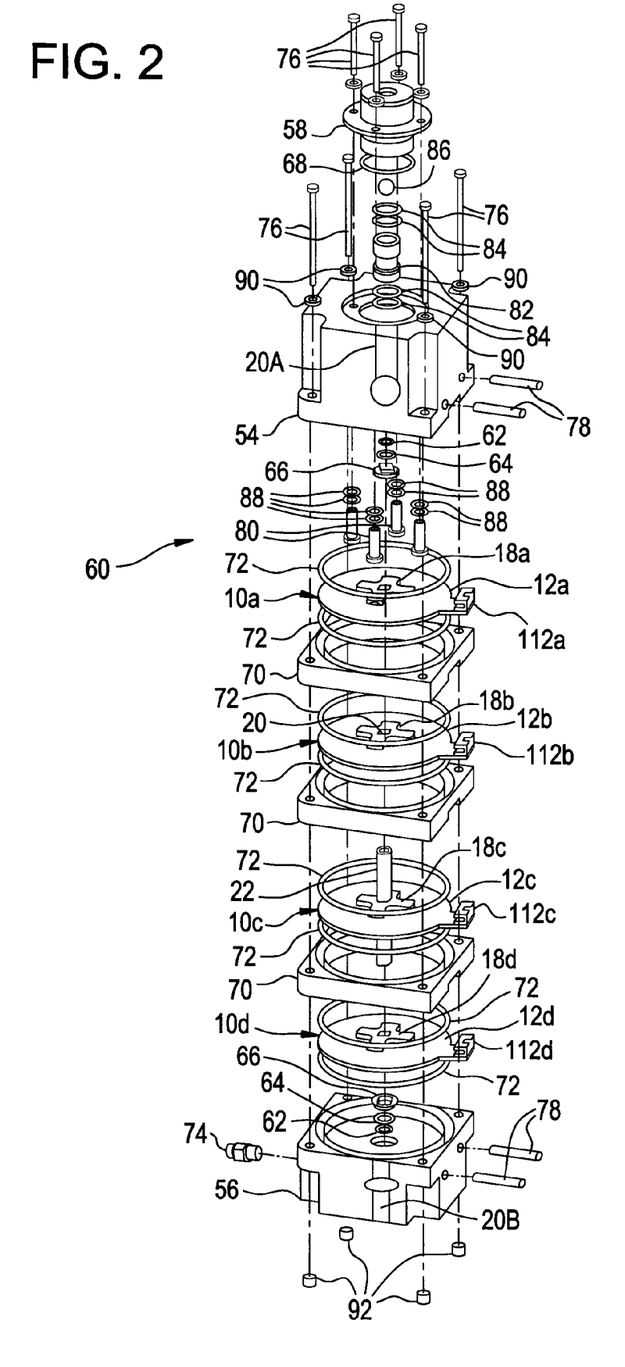
FIG. 2 is an exploded view of a modular fluorometer made in accordance with the present invention where there are four units present.
Figure 3:
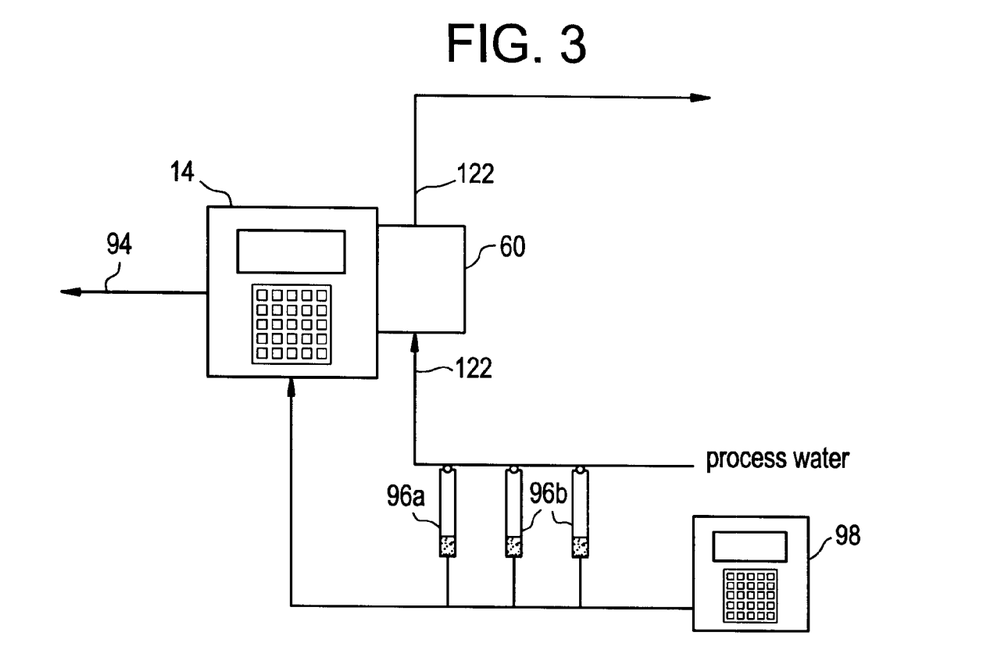
FIG. 3 is a schematic illustration of the control system of the present invention, wherein the controller is shown in this figure as a "black box".

Turning to FIG. 1, a modular fluorometer unit 10 is illustrated in an exploded view which includes a printed circuit board assembly 12 which is connected to a controller 14 (see FIG. 3). The printed circuit board assembly 12 includes an opening 16 which accommodates a body 18. The body 18 includes a channel 20 for accommodating an optically appropriate cell 22 (see also FIGS. 2 and 4). A sample of water flows through channel 20 into optically appropriate cell 22.

The printed circuit board (PCB) assembly can be fabricated by people of ordinary skill in the art of printed circuit boards and fluorometers. Printed circuit board assemblies useful in this device must be fabricated to allow powering of the components of the fluorometer, which include drivers for the excitation sources and amplifiers to perform current-to-voltage conversion and signal amplification from the photodetectors. Circuitry to manipulate the signals and communicate the magnitude of the signals is also integral to the PCB. Additional circuitry to measure the temperature transistor and/or the status of the flowswitch may be included.

Figure 4:
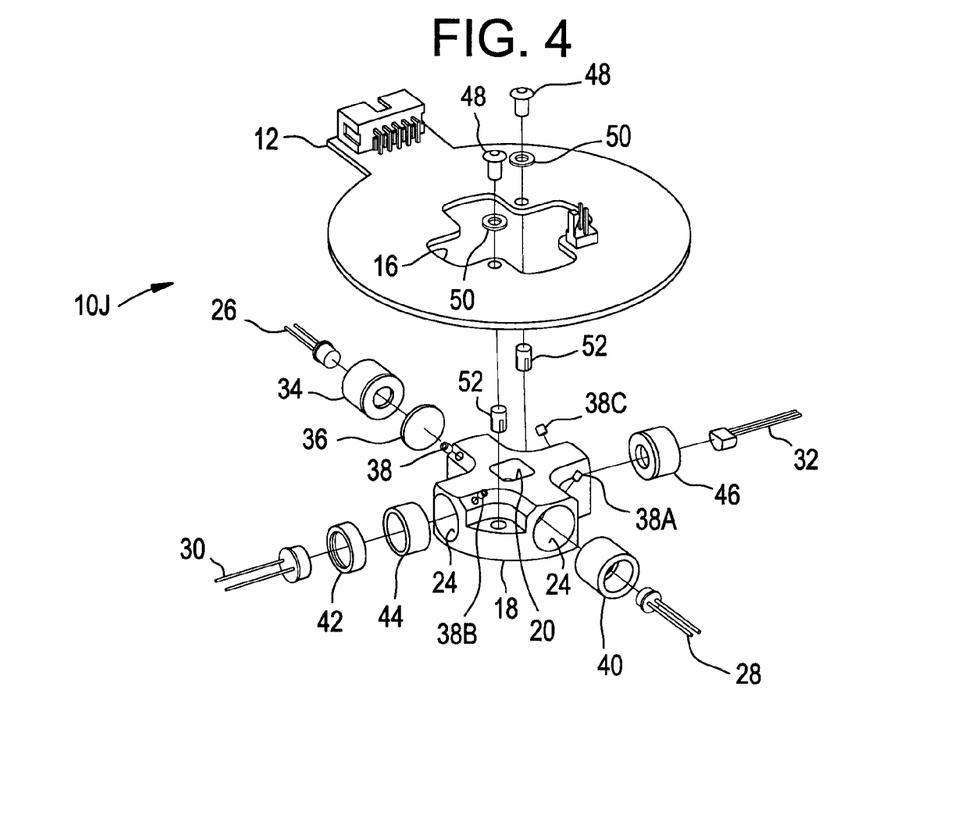
FIG. 4 is an exploded view of a second embodiment of one unit of a module fluorometer made in accordance with the present invention.

The body 18 includes four side openings 24 (only two of which are visible in FIG. 1) which side openings 24 are coplanar and oriented at 90° angles to each other, for accommodating a light source 26, a reference detector 28, and two emission detectors 30 as shown in FIG. 1. Because only one emission detector 30 is required, an alternative embodiment of a modular fluorometer unit 10J is possible and is shown in FIG. 4. In FIG. 4 this configuration is shown to include one emission detector 30 and an alternative component, such as a temperature sensor 32.

The light source 26 is preferably a light emitting diode and can be housed in a bushing 34 which fits inside its respective side opening 24. An excitation filter is optionally included in this configuration. In FIG. 1, an excitation filter 36 is positioned between the light source 26 and the optically appropriate cell 22. The bushing 34 is held in place by set screw 38.

Light emitting diodes (LEDs) are commercially available from Nichia Corporation, 3775 Hempland Road, Mountville, Pa., 17554 USA, (717) 285-2323.

If the spectral range of light source 26 is sufficiently narrow or monochromatic, or the fluorophore stokes shift is sufficiently large so that there is no spectral overlap between the excitation light spectrum of light source and the emission spectrum of the fluorophore, then excitation filter 36 is optional. A monochromatic light source can be a laser. Lasers are commercially available from Nichia.

Reference detector 28 is positioned outside the optically appropriate cell 22. Preferably, reference detector 28 is aligned directly opposite said light source 26. A second bushing 40 is used to hold the reference detector 28 in place inside the side opening 24 and adjacent to the optically appropriate cell 22. A second set screw 38A holds the second bushing 40 in place. Emission detectors 30 are positioned coplanarly with respect to light source 26 and reference detector 28. Preferably emission detectors 30 can be positioned at angles from 2 degress to 179 degrees relative to light source 26 and relative to reference detector 28. Preferably, emission detectors 30 are positioned at about a 90 degree angle relative to light source 26 and reference detector 28 though they. The detectors 30 are held in place inside the side openings 24 by third bushings 42. An optical filter 44 is positioned between each detector 30 and the optically appropriate cell 22. Third set screws 38B hold the third bushings 42 in place.

Reference detectors and emission detectors are preferably photodiodes that are commercially available from Hamamatsu Corporation, 360 Foothill Road, Bridgewater, N.J. 08807, (800) 524-0504.

It will be noted that a single detector 30 may be employed as shown in FIG. 4 in contrast to the dual detector configuration of FIG. 1. In the event a single detector 30 is employed as shown in FIG. 4, the remaining side opening 24 may remain unused or may accommodate a temperature sensor 32 or other component. In FIG. 4, a fourth bushing 46 is used to hold the temperature sensor 32 in place inside the side opening 24. Fourth set screw 38C is used to hold fourth bushing 46 in place.

Referring to FIGS. 1 and 4 together, fasteners 48, washers A 50 and inserts 52 are used to secure the printed circuit board assembly 12 to the body 18. In a preferred embodiment, fasteners 48 are screws, and reference detectors 28 and emission detectors 30 are photodiodes. The temperature sensor 32 may be any commercially available temperature sensor. Preferably temperature sensor 32 is a transistor. Transistors are commercially available from available from Digi-key Corporation, 701 Brooks Avenue South, Thief River Falls, Minn. 56701-0677, (800) 344-4539.

As shown in FIG. 2, modular fluorometer units 10 as shown in FIGS. 1 and 4 can be stacked one on top of another to form a modular fluorometer 60 capable of detecting anywhere from one to sixteen different fluorophore species one at a time or simultaneously. The limitation of sixteen different fluorophore species is based on the fact that the spectrum encompassing the excitation wavelengths and emission wavelengths from about 200 nm to about 1200 nm can practically be broken down into only a maximum of about 16 separate segments that can be separately detected using the instant claimed fluorometer.

As shown in FIG. 2, first modular fluorometer unit 10a, second modular fluorometer unit 10b, third modular fluorometer unit 10c and fourth modular fluorometer unit 10d are stacked one on top of each other. First modular fluorometer unit 10a, second modular fluorometer unit 10b, third modular fluorometer unit 10c and fourth modular fluorometer unit 10d all contain two emission detectors 30 each with each emission detector 30 being positioned behind an optical filter 44. Each optical filter 44 is capable of permitting passage of a different light spectrum having a different maximum wavelength through the optical filter 44 to the emission detector 30, therefore modular fluorometer 60 is capable of detecting eight different fluorophores.

Thus, the embodiment illustrated in FIG. 2 is capable of detecting anywhere from one to eight different fluorophores, depending upon the particular arrangement employed. For example, measuring two fluorophores with the same modular fluorometer usit requires that the excitation spectra for each fluorophore be similar. Of course, additional molecular fluorometer units 10 may be added to modular fluorometer 60 to increase the number of fluorophore species that modular fluorometer 60 can detect.

The fluorometer units are mounted to the controller 14 by suitable fasteners (not shown). A gasket (not shown) is placed between the modular fluorometer 60 and controller 14.

Controller 14 is available from Tecnova, 1486 St. Paul Ave., Gurnee, Ill. 60031 (847) 662-6260.

The modular fluorometer 60 is further connected to controller 14 by a communication cable (not shown) that enables the controller 14 to electronically communicate with each modular fluorometer unit 10. A suitable communication protocol must be selected in order to operate the modular fluorometer 60. Suitable standard communication protocols include, but are not limited to, RS-232, $I^2C$, CAN, TCP/IP and a standard RS-485 serial communication protocol. The preferred communication protocol is a standard RS-485 serial communication protocol. It is also possible to use a wireless communication protocol between the modular fluorometer 60 and controller 14. One such suitable wireless communication protocol is Bluetooth.

Regardless of the number of modular fluorometer units 10 included in the modular fluorometer 60, each modular fluorometer unit 10 is connected in series using the communication cable (not shown), with said communication cable being connected to the printed circuit board 12 at connection port 112. FIG. 2 shows one possible configuration, with four modular fluorometer units 10a, 10b, 10c and 10d included. Each module fluorometer unit 10a, 10b, 10c, and 10d, is serially connected to the single communication cable (not shown). The communication cable is attached to $1^{st}$ connection port 112a, $2_{nd}$ connection port 112b, $3^{rd}$ connection port 112c and $4^{th}$ connection port 112d. The termination of the communication cable is one of the inputs to controller 14 as previously described.

In all instances considered for the modular fluorometer 60, the communication cable (not shown) that is used to connect each modular fluorometer unit 12 to controller 14 contains a connector (not shown) for each modular fluorometer unit present and an additional connector (not shown) to link the communication cable with controller 14. In a preferred configuration where modular fluorometer (60) consists of four modular fluorometer units 12, the communication cable (not shown) would have five connectors (not shown).

In FIG. 2, first modular fluorometer unit 10a, second modular fluorometer unit 10b, third modular fluorometer unit 10c and fourth modular fluorometer unit 10d are sandwiched between an upper housing 54 and a lower housing 56. The optically appropriate cell 22 intersects each upper housing 54 and lower housing 56. To protect the various electrical components of the modular fluorometer 60, primary seals are shown at 62 and secondary seals are shown at 64. Primary seals 62 and secondary seals 64 are held in place by gasket 66. An O-ring 68 is provided to create a seal between retainer 58 and upper housing 54.

Channel 20A to channel 20B runs from top to bottom through the entire modular fluorometer 60. Upper channel 20A intersects upper housing 54. Lower channel 20B also intersects lower housing 56.

Optically appropriate cells 22 are present in each modular fluorometer unit.

Adapter plates 70 are positioned between adjacent modular fluorometer units 10a and 10b, 10b and 10c, and 10c and 10d. Seals shown at 72 are provided on either side of the first printed circuit board 12a, second printed circuit board 12b, third printed circuit board 12c, and fourth printed circuit board 12d to provide a seal between the printed circuit boards and either upper housing 54, lower housing 56 or an adapter plate 70. A check valve 74 is provided to allow introduction of cleaning and/or calibration fluids.

The modular fluorometer 60 is held together by a plurality of threaded fasteners 76. Female threaded members 80 are used to secure retainer 58 against upper housing 54. Threaded studs 78 are used to secure modular fluorometer 60 to controller 14 (see FIGS. 2 and 3).

Upper channel 20A passes through a flow cell 82 that is sealed within retainer 58 by the first O-rings 84. A ball 86 is positioned within the flow cell 84. Preferably ball 86 is made of nickel-coated brass. Second O-rings 88 are used to effectuate a seal between female threaded members 80 and the underside of the retainer 58. Washers B, shown at 90 are positioned between threaded fasteners 76 and upper housing 54. Threaded fasteners 76 are connected to threaded inserts 92.

The construction of the modular fluorometer 60 shown in FIG. 2 can be achieved by a variety of methods and embodiments, only one of which is shown in FIG. 2. The preferred configuration is the one that is illustrated in FIG. 3, and in this configuration, the flow cell 82 and ball 86 will not allow fluid to flow properly thorough the fluorometer if the fluorometer is inverted. However, should modular fluorometer 60 be inverted completely or tilted at any angle between 0° and 360°, it is still capable of functioning, providing a flow valve regulator is used that is independent of gravity. Such flow cell regulators are known in the art.

Turning to FIG. 3, as previously described, modular fluorometer 60 (shown as a "black box" in this figure) is connected to controller 14. The output signal 94 from controller 14 may, in turn, be connected to a plurality of devices, which may include pumps that control the cooling system or electrically activated valves. Further, process water stream 122 may be sampled at a plurality of points indicated at 96a, 96b and 96c to provide additional information to controller 14 such as pH, the amount of total dissolved solids, conductivity, or the oxidation-reduction potential of the process water. This information, in addition to the information provided by modular fluorometer 60 may be used by controller 14 to control the water industrial water system.

There also exists in controller 14 provisions for isolated, multiple analog inputs with. These inputs provide information on their signal magnitude via 4–20 mA connections. Said signals, being read by the analog inputs, can be used in the control logic of controller 14 to provide additional levels of control to an industrial water system. In a preferred embodiment, controller 14 has twenty (20) discrete analog inputs(not shown).

As stated in the preceding paragraph, the controller has the capability of processing signals available over a 4–20 mA communication line. These signals do not have to come from the fluorometer, they can originate from other analytical devices. Therefore, the controller is capable of processing signals from analytical devices that measure system factors including, but not limited to:

pH;

conductivity;

oxidation-reduction potential or "ORP";

chemical monitors for species such as calcium, magnesium, total hardness, iron, copper, chloride, sulfate, manganese, aluminum, silica, alkalinity and ammonia;

additional chemical monitors of treatment actives such as dispersant polymer, zinc, molybdate, phosphate, condensed inorganic phosphates, phosphonates and triazoles; turbidity;

total suspended solids;

process leaks;

free residual & total oxidant/halogen/chlorine;

water temperatures;

process-side temperatures at various places in the system;

fluid flowrates on the water-side and/or process-side;

fluid velocities;

fluid pressures and differential pressures on the water-side and/or process-side;

chemical inventories/usage;

chemical pumping rates;

blowdown rates;

makeup water rates;

corrosion monitors; and fouling/deposit monitors;

microbiological indicators; and light absorbance of substances in water.

In addition to the analog inputs, the controller has a sufficient number of analog outputs such that it can control other equipment, besides the fluorometer. Thus the controller is capable of operating an entire industrial water system.

A secondary controller 98 can optionally be used to control the rate of additive chemical added to the process water. Secondary controller 98 if used, may be linked to controller 14 as well. Preferably secondary controller 98 would be controlling an inert TRASAR® system, with said inert TRASAR® system being commercially available from Nalco Chemical Company, One Nalco Center, Naperville Ill. 60563, (630) 305-1000.

Accordingly, the present invention provides a means for detecting and monitoring the presence of a plurality of fluorophores in an industrial water system using a modular fluorometer apparatus.

Regarding the description of the fluorophores capable of being detected by the instant claimed fluorometer, it is necessary to note that in order to be detectable by the instant claimed modular fluorometer, the fluorophore must be capable of absorbing light in the wavelengths of from about 200 nm to about 1200 nm and emitting it at a slightly longer wavelength. Preferably, the fluorophores absorb light in the wavelengths of from about 350 nm to about 800 nm.

Each modular fluorometer unit 10 is compact, inexpensive to manufacture and rugged. In constructing each modular fluorometer unit 10, the emission detectors 30 are preferably photodiodes, the light sources 26 are preferably light emitting diodes and reference detectors 28 are also preferably photodiodes. As shown in FIG. 2, anywhere from one to sixteen modular fluorometer units 10 may be stacked and, as shown in FIGS. 1 and 4, each fluorometer 10 may include one or two optical detectors 30.

The setup of the fluorometer, regarding excitation and emission settings, as well as filter settings is within the ability of a person of ordinary skill in the art of fluorometry.

The instant claimed modular fluorometer can be used with water from any water system including natural water and water used in industrial water systems. Industrial water systems include, but are not limited to, cooling tower water systems (including open recirculating, closed and once-through systems); petroleum wells, downhole formations, geothermal wells and other oil field applications; boilers and boiler water systems; mineral process waters including mineral washing, flotation and benefaction; paper mill digesters, washers, bleach plants and white water systems; black liquor evaporators in the pulp industry; gas scrubbers and air washers; continuous casting processes in the metallurgical industry; air conditioning and refrigeration systems; industrial and petroleum process water; indirect contact cooling and heating water, such as pasteurization water; water reclamation and purification systems; membrane filtration water systems; food processing streams (meat, vegetable, sugar beets, sugar cane, grain, poultry, fruit and soybean); and waste treatment systems as well as in clarifiers, liquid-solid applications, municipal sewage treatment and industrial or municipal water systems.

The third aspect of the instant claimed invention is a method of controlling an industrial water system comprising using the modular fluorometer wherein said modular fluorometer further comprises a controller with said controller comprising isolated analog inputs such that the controller is capable of using the measured fluorescent signals provided by the modular fluorometer and the other analog inputs to control an industrial water system.

The instant claimed fluorometer and controller are capable of functioning to control a cooling water system, as described and claimed in U.S. patent application Ser. No. 09/562,397, entitled USE OF CONTROL MATRIX FOR COOLING WATER SYSTEMS CONTROL, filed May 1, 2000, now pending, which is herein incorporated by reference in its entirety.

The instant claimed fluorometer and controller are capable of functioning to control a boiler, as described and claimed in U.S. patent application Ser. No. 09/563,085, entitled USE OF CONTROL MATRIX FOR BOILER CONTROL, filed May 1, 2000, now pending, which is herein incorporated by reference in its entirety.

In addition to the above described method, the modular fluorometer of the instant claimed invention is particularly useful in conducting the method described and claimed in a pending U.S. Patent Application, MEASUREMENT AND CONTROL OF SESSILE AND PLANTONIC MICROBIOLOGICAL ACTIVITY IN INDUSTRIAL WATER SYSTEMS, U.S. patent application Ser. No. 09/475,585, filed Dec. 30, 1999, and herein incorporated by reference in its entirety. When using the instant claimed modular fluorometer to conduct the method described and claimed in U.S. patent application Ser. No. 09/475,585, the modular fluorometer unit used should either contain two emission detectors in order to detect the fluorescent signal from both the reacted and unreacted fluorogenic dye simultaneously or at least two modular fluorometer units should be used so that one modular fluorometer unit could detect the signal from the unreacted fluorogenic dye and the other could detect the signal from the reacted fluorogenic dye.

The following example is presented to be illustrative of the present invention and to teach one of ordinary skill how to make and use the invention. This example is not intended to limit the invention or its protection in any way.

EXAMPLES

Example 1

A standard laboratory pilot cooling tower (PCT) was configured to simulate operation of a light industrial cooling system. A chemical treatment program was formulated that contained typical cooling water treatment species. This program was a combination of 50 wt. % water, 4 wt. % phosphonobutanetricarboxylic acid (sodium salt), 3.5 wt. % hydroxyethylidenediphosphonic acid (potassium salt), 3 wt. % acrylate/acrylamide polymer, 3 wt. % tolyltriazole (sodium salt), 0.1 wt. % pyrenetetrasulfonic acid (sodium salt) and 0.05 wt. % fluorescein (sodium salt). This solution was adjusted to a pH of 13 with 50% sodium hydroxide and used without further processing. The PCT was operated with Chicago, Ill. U.S.A. tap water as a makeup source and the cycles of concentration were set to maintain 4 cycles.

The modular fluorometer used in this experiment comprised tow modular fluorometer units and a controller. The first modular fluorometer unit was configured using a light-emitting diode (LED) with emission centered at 365 nm with a current of 10 mA. Optical filter 44 was used to select the fluorescence emission at 405 nm, which was subsequently detected by an emission detector. Additionally, the first modular fluorometer unit was configured with a temperature sensor and a reference detector.

The second modular fluorometer unit was configured with a light-emitting diode with emission centered at 450 nm. The second modular fluorometer unit used an optical filter to select fluorescence emission at 515 nm, which was subsequently detected by emission detector 30. The second modular fluorometer unit also contained an emission detector.

Both modular fluorometer units were calibrated using a two-point routine using distilled water as the zero point and a 100 ppm solution of the chemical treatment program as the upper point. The controller was configured with software to measure the fluorescence of each modular fluorometer unit independently. The controller also had a sufficient number of analog inputs/outputs such that it was able to provide control of chemical product addition to the PCT using a setpoint of 50±1 ppm based on the measured fluorescent signal of pyrenetetrasulfonic acid (sodium salt) as measured by the first modular fluorometer unit. The chemical product level was controlled using an on/off strategy where a chemical feed pump was electrically controlled by the modular fluorometer controller. If the measured fluorescent signal fell below 49 ppm, the chemical feed pump was actuated and run until the chemical level reached 51 ppm, when the pump was turned off. Additionally, the modular fluorometer controller was configured to control the blowdown pump of the PCT. The controller was set to turn on (actuate) the blowdown pump if the % difference between the two fluorometric signals was greater than 15% and turn it off if the difference was less than 15%. During system blowdown, the water level in the PCT was maintained using fresh Chicago tap water as a makeup source. Therefore, as the system was blown-down via the blowdown pump and fresh water was added the overall concentration of fluorophore present in the volume of the system was decreased as expected, due to dilution of the cooling water by fresh water added as make-up water. This decrease resulted in actuation of the chemical feed (pyrenetetrasulfonic acid (sodium salt) signal) to maintain 50±1 ppm of chemical product. This cycling continued until the appropriate control levels were reached.

Figure 5:
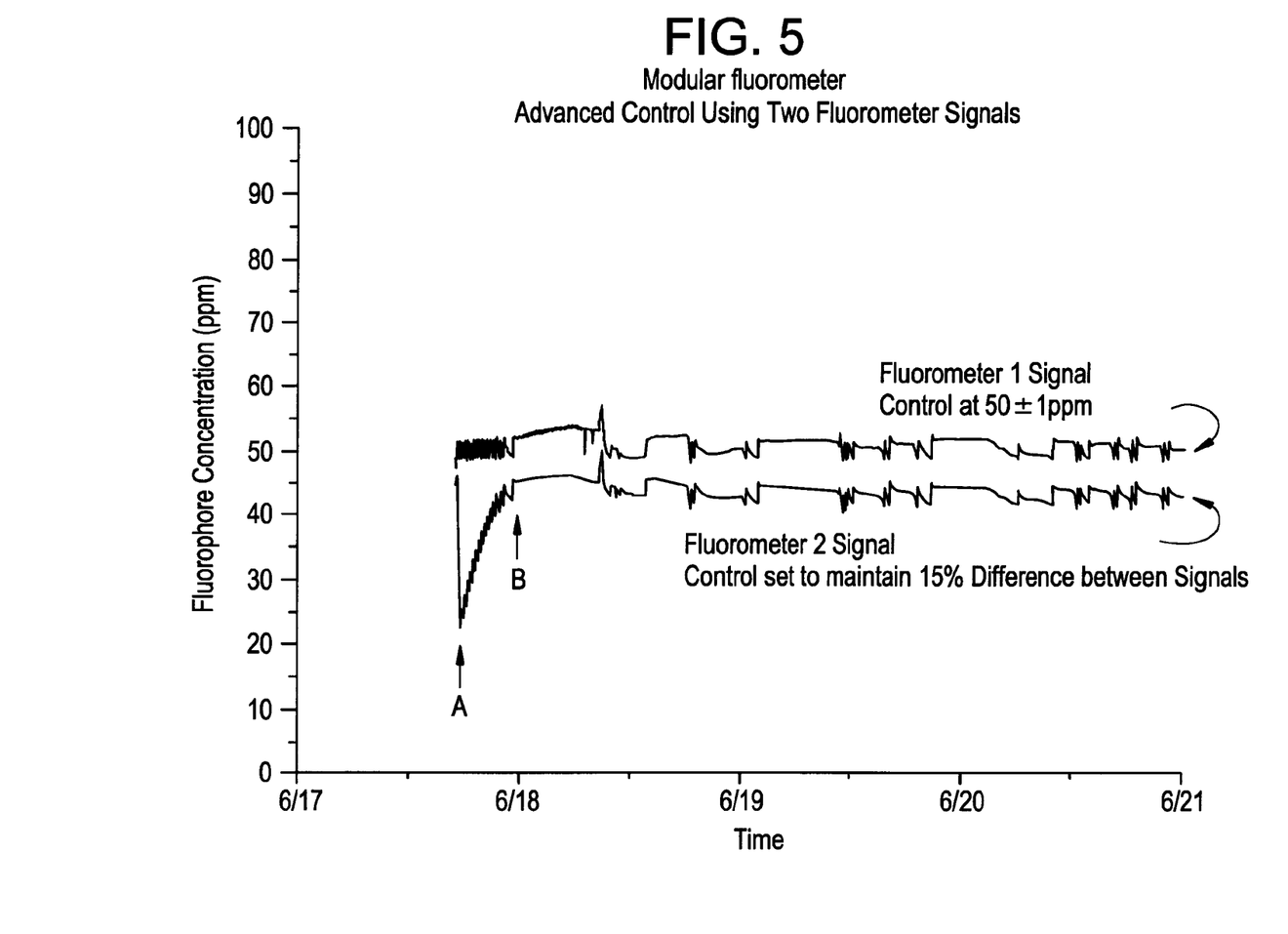
FIG. 5 is a plot of "Modular Fluorometer Advanced Control Using Two Fluorometer Signals" which has a y-axis labeled "Fluorophore concentration in ppm" and an x-axis labeled "Time".

Control of the PCT is illustrated in FIG. 5. Using the modular fluorometer made it possible for the controller to maintain control of both the first modular fluorometer unit signal and the second modular fluorometer unit signal at a 15% difference in signals (signal 2 was 85% of signal 1). Prior to point A this was the condition of the cooling water system. At point A, a 1 mL aliquot of 100 ppm bleach was added to the system. This addition depleted the fluorescent signal of fluorescein that is being measured by second modular fluorometer unit. At this point the difference in the fluorometric signals was forced to be greater than 15%, so that the blowdown pump of the system was actuated. The system was blown down and the online chemical feed control maintained a product level of 50±1 ppm control while the fresh chemical was added to the system. At point B the system had re-established the desired level of control. At that point the PCT system was operated to maintain a 15% difference in the fluorometric signals.

It should be understood that various changes and modifications to the presently preferred embodiments described herein will be apparent to those skilled in the art. Such changes and modifications can be made without departing from the spirit and scope of the present invention and without diminishing its attendant advantages. It is therefore intended that such changes and modifications be covered by the appended claims.

What is claimed is:

1. A modular fluorometer comprising:
   from at least two modular fluorometer units to no more than sixteen modular fluorometer units, with each modular fluorometer unit comprising:
   a) a channel comprising an optically appropriate cell through which a water sample flows;
   b) a light source positioned outside said optically appropriate cell;
   c) an optional excitation filter positioned between the light source and the optically appropriate cell;
   d) a reference detector positioned outside the optically appropriate cell;
   e) an emission detector positioned outside the optically appropriate cell; and
   f) an optional emission filter positioned between said emission detector and said optically appropriate cell;
   wherein said optically appropriate cells through which said water sample flows are aligned such that only one channel through which a water sample flows exists in said fluorometer.

2. The modular fluorometer of claim 1 wherein said light source is a light emitting diode.

3. The modular fluorometer of claim 1, wherein said reference detector and said emission detectors are both photodiodes and said emission detector is positioned at a 90° angle relative to said light source and said reference detector.

4. The modular fluorometer of claim 1, wherein said reference detector is aligned directly opposite said light source.

5. The modular fluorometer of claim 1, further comprising a controller.

6. The modular fluorometer of claim 5, wherein said controller comprises isolated analog inputs such that the controller is capable of using the measured fluorescent signals provided by the modular fluorometer and the other analog inputs to control an industrial water system.

7. The modular fluorometer of claim 6, wherein said industrial water system is a cooling water system.

8. A method of detecting the presence of one or more fluorophore species in a water sample wherein each of said fluorophore species emit light of different emission spectra after being illuminated with light defined by specific excitation spectra, the method comprising the steps of:
   a) providing a modular fluorometer, said modular fluorometer comprising:
   from at least two modular fluorometer units to no more than sixteen modular fluorometer units, with each modular fluorometer unit comprising:
   i) a channel comprising an optically appropriate cell through which a water sample flows;
   ii) a light source positioned outside said optically appropriate cell;
   iii) an optional excitation filter positioned between the light source and the optically appropriate cell;
   iv) a reference detector positioned outside the optically appropriate cell;
   v) an emission detector positioned outside the optically appropriate cell;
   vi) an optional emission filter positioned between said emission detector and said optically appropriate cell;

wherein said optically appropriate cells through which said water sample flows are aligned such that only one channel through which a water sample flows exists in said fluorometer; wherein said modular fluorometer has sufficient units to detect the presence of each fluorophore species in said water sample;

b) moving a water sample comprising the fluorophores through each respective optically appropriate cell;

c) illuminating said water sample with the respective light source in each unit; and d) detecting each fluorophore species by detecting the emission spectra with the respective emission detectors in each modular fluorometer unit.

9. The method of claim 8 wherein said reference detector is aligned directly opposite said light source and said emission detector is positioned at a 90° angle relative to said light source and said reference detector.

10. The method of claim 8 wherein said modular fluorometer further comprises a controller.

11. The method of claim 10 wherein said controller comprises isolated analog inputs and outputs such that the controller is capable of using the measured fluorescent signals provided by the modular fluorometer and input from other analytical devices to control an industrial water system.

12. The method of claim 11 wherein said industrial water system is a cooling water system.

13. A method of controlling an industrial water system, wherein the water in said industrial water system comprises one or more fluorophore species wherein each of said fluorophore species emit light of different emission spectra after being illuminated with light defined by specific excitation spectra, the method comprising the steps of a) using a modular fluorometer wherein said modular fluorometer comprises
from at least two modular fluorometer units to no more than sixteen modular fluorometer units, with each modular fluorometer unit comprising:

i) a channel comprising an optically appropriate cell through which a water sample flows;

ii) a light source positioned outside said optically appropriate cell;

iii) an optional excitation filter positioned between the light source and the optically appropriate cell;

iv) a reference detector positioned outside the optically appropriate cell;

v) an emission detector positioned outside the optically appropriate cell;

vi) an optional emission filter positioned between said emission detector and said optically appropriate cell;

wherein said optically appropriate cells through which said water sample flows are aligned such that only one channel through which a water sample flows exists in said fluorometer;

wherein said modular fluorometer further comprises a controller;

with said controller comprising isolated analog inputs such that the controller is capable of using the measured fluorescent signals provided by the modular fluorometer and input from other analytical devices to control an industrial water system;

b) moving a water sample comprising the fluorophores through each respective optically appropriate cell;

c) illuminating said water sample with the respective light source in each unit;

d) detecting each fluorophore species by detecting the emission spectra with the respective emission detectors in each modular fluorometer unit; and e) using the measured fluorescent signals provided by the modular fluorometer and input from other analytical devices to control an industrial water system.

14. The method of controlling an industrial water system of claim 13 wherein said industrial water system is a cooling water system.

* * * * *